United States Patent [19]

Van Leeuwen et al.

[11] Patent Number: 6,001,878

[45] Date of Patent: *Dec. 14, 1999

[54] METHOD OF TREATING DISORDERS OF THE ANIMAL OR HUMAN BODY BY ADMINISTERING AMINO ACIDS

[76] Inventors: Paulus Aloisius Marie Van Leeuwen, Haya van Somerenlaan 30, L-1187 RB Amstelveen; Alexander Petrus Jacobus Houdijk, Van der Ghiessenstraat 25, NL-1181 RS Amstelveen, both of Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 08/669,484

[22] PCT Filed: Jan. 11, 1995

[86] PCT No.: PCT/NL95/00015

§ 371 Date: Oct. 10, 1996

§ 102(e) Date: Oct. 10, 1996

[87] PCT Pub. No.: WO95/18608

PCT Pub. Date: Jul. 13, 1995

[30] Foreign Application Priority Data

Nov. 1, 1994 [EP] European Pat. Off. .............. 94200042

[51] Int. Cl.⁶ .................................................. A61K 31/195
[52] U.S. Cl. ............................................................ 514/563
[58] Field of Search ...................... 514/561, 563

[56] References Cited

U.S. PATENT DOCUMENTS

| | | | |
|---|---|---|---|
| 4,687,782 | 8/1987 | Brantman | 514/561 |
| 4,987,123 | 1/1991 | Masaki et al. | 514/19 |
| 5,157,022 | 10/1992 | Barbul . | |
| 5,217,997 | 6/1993 | Levere et al. . | |
| 5,504,072 | 4/1996 | Schmidl et al. | 514/21 |

FOREIGN PATENT DOCUMENTS

| | | |
|---|---|---|
| 0 329 879 | 8/1989 | European Pat. Off. . |
| 0 401 056 | 12/1990 | European Pat. Off. . |
| 0 441 119 | 8/1991 | European Pat. Off. . |
| 0 494 848 | 7/1992 | European Pat. Off. . |
| 91 10 794 | 12/1991 | Germany . |
| 61-186320 | 8/1986 | Japan . |
| 5-229940 | 9/1993 | Japan . |
| WO 87/01589 | 3/1987 | WIPO . |
| WO 91/07188 | 5/1991 | WIPO . |
| WO 92/04895 | 4/1992 | WIPO . |

*Primary Examiner*—Raymond Henley, III
*Attorney, Agent, or Firm*—Young & Thompson

[57] ABSTRACT

The invention relates to the use of glutamine or a glutamine equivalent for the treatment of disease states where there is a decreased blood flow to the liver or where there are low arginine plasma levels. Such disease states comprise systemic inflammation, high plasma arginase level, bacteremia, jaundice, liver transplantation, increased cytokine production or liver steatosis.

4 Claims, No Drawings

METHOD OF TREATING DISORDERS OF THE ANIMAL OR HUMAN BODY BY ADMINISTERING AMINO ACIDS

This is a 371 of PCT/NL95/00015 filed Jan. 11, 1995.

The invention relates to a method of treating disorders of the animal or human body which require increasing blood flow to intestinal organs as well as to a method of treating disorders which can be treated by administering arginine.

The present invention relates in particular to the use of glutamine in the diseased state where there is a decreased blood flow to the liver or where there are low arginine plasma levels.

The splanchnic bed consists of several organs all of which drain into the portal vein. A liver receives its blood supply from both the portal vein and the hepatic arteria. 70–80% of the blood flow to the liver is received by the portal vein and therefore most of the nutrients and oxygen is taken out of the blood coming from the portal vein and is thus insufficient during a decrease in blood flow. Glutamine is capable of increasing blood flow through the liver by increasing splanchnic blood flow.

During periods of decreased blood flow (systemic inflammation, hypovolemia, cardiac shock, decreased peripheral resistance), blood flow to the liver is lower.

After normalisation of the blood flow, the liver passes into the stage of reperfusion damage which compromises blood flow in the liver, which further deteriorates liver function. Blood flow then is mostly maintained in the liver by increased nitric oxide (NO) production. Arginine is the substrate for NO. When there is an increased demand for NO, there may not be sufficient arginine as a substrate, or there may be an increased demand for arginine.

Those diseased states are during low arginine level e.g. endotoxemia, systemic inflammation, high arginase content in plasma, bacteremia, obstructive jaundice, other types of jaundice, liver transplantation, liver resection, inflammatory bowel disease, transplantation in general, increased cytokine production, steatosis of the liver.

Thus the invention is specifically directed at the use of glutamine or a glutamine equivalent for preparing a medicinal or nutritional composition for the treatment of diseased states where there is a decreased blood flow to the liver or where there are low arginine plasma levels. These diseased states can be those mentioned above, especially endotoxemia, systemic inflammation, high plasma arginase level, bacteremia, jaundice, liver transplantation, liver resection, inflammatory bowel disease, or increased cytokine production.

A glutamine equivalent is understood to be a substance which can be converted to glutamine, such as a glutamine dipeptide or a 2-acylaminoglutaric acid monoarnide. The glutamine or glutamine equivalent in the medicinal or nutritional composition may be supplemented by arginine or an arginine equivalent, e.g. to an amount of 0–50%, especially 1–25% of the combined amounts of glutamine and arginine and their equivalents. The medicinal or nutritional composition preferably contains an amount of glutamine or glutamine equivalent such as to provide a daily glutamine dosage of 0.2–4 g/kg body weight. This means that glutamine or its equivalent is administered in amount of e.g. 10–200 g/day for a subject having a body weight of 50 kg, or 20–400 g/day for a subject having a body weight of 100 kg. Below, the levels to be used are given on the basis of an assumed average body weight of 75 kg, but adaptations can be made as necessary.

The medicinal and nutritional compositions according to the invention are preferably formulated as enteral compositions. The composition may be a complete artificial food, i.e. which does not require additional food, or a food supplement. The further components of a complete food are preferably based on the recommended daily allowances (RDA) as generally accepted; the protein fraction may be based on a protein source rich in glutamine, or its hydrolysates. A supplement may be a glutamine contrate, e.g. obtained by hydrolysis of raw materials rich in glutamine, such as wheat protein. The enteral food may then be obtained by mixing, before use, of the concentrate with a basic food, e.g. according to the RDA. The composition preferably is liquid composition for oral or cathereterised administration. Preferably the composition is a nutritional composition which also contains carbohydrates, proteins, lipids, and especially fibres, in amounts that are sufficient for meeting a minimum daily nutritional requirement.

The invention also concerns novel nutritional compositions suitable for improving liver function, containing, as a daily dosage unit, 12–300 g of glutamine or a glutamine equivalent, together with an amount of carbohydrates, proteins, lipids, vitamins, minerals and vegetable fibres, which is sufficient for meeting a minimum daily nutritional requirement. The nutritional composition preferably contains, as a daily dosage unit, especially 15–300, more preferably 16–150, more in particular 30–100 g of glutamine or a glutamine equivalent. The amount of glutamine or equivalent thereof can also be given with reference to the total weight of the composition. In case of liquid compositions, which are preferred, the amount of glutamine is in particular from 7 to 150 g/l, especially from 15 to 150, more in particular 25 to 75 g/l.

Especially preferred are nutritional composition containing at least 10 g of vegetable fibres and/or 5 g of inulin (indigestible carbohydrate) on a daily basis. Fibres and/or inulin may be used in amounts up to e.g. 90 g per day.

Where the amount of glutamine is too high to be able to be homogeneously mixed with the other components, it is advantageous to prepare a nutritional composition, wherein at least a part (e.g. $\geq 75\%$) of the glutamine is in a package form separate of the major part (e.g. $\geq 75\%$) of the composition. The separate packages can then be combined before use. In such a way, stability problems can be overcome.

The invention also provides a method of treating disorders of the animal or human body which can be treated by administering arginine, such as reduction of blood cholesterol levels (cf. U.S. Pat. No. 5,157,022) or treatment of vascular resistance disorders (cf. U.S. Pat. No. 5,217,997), comprising administering an effective amount of glutamine or a glutamine equivalent. An effective amount preferably is an amount which is greater than the glutamine level in a normal animal or human diet as indicated above, e.g. between 0.2 and 4 g/kg b.w. day.

The invention is also concerned with the use of glutamine for the treatment of adverse effects associated with impaired reticulo-endothelial system (RES) function and specifically for the treatment of adverse effects associated with impaired RES function resulting from insults to the liver. The RES, also called the mononuclear phagocyte system (MPS) consists of tissue macrophages and blood monocytes. The major sites of RES intravascular activity are located in the liver and spleen, which comprise about 85% and 10%, respectively, of total body activity. The Kupffer cells and the endothelial cells of the liver are capable of scavenging antigens and endotoxins from the portal vein and the systemic circulation. Kupffer cells reside in the liver for a few weeks and are then replaced by circulating monocytes that subsequently differentiate into new Kupffer cells. In response to injury or liver resection, Kupffer cells can divide and proliferate locally to restore the hepatic function. It was found that the administration of relatively high levels of glutamine has a beneficial effect on the restoration of this type of liver functioning.

The combined use of glutamine and alanine for the treatment of alcohol intoxication of the liver is described in EP-A-0,329,879. However, this reference does not contain any indication that glutamine, especially glutamine alone, could be useful in treating diseased states that are associated with a decreased liver blood flow. Moreover, the dosages suggested in EP-A-0,329,879 are in the order of 1–20 g per person per day, which is well below the doasges contemplated according to the present invention.

Most other suggested uses for glutamine as a medicament relate to the use in parenteral administrations, such as in connection with improving nitrogen balance, prevention of gut mucosal atrophy and subsequent bacterial translocation and stimulation of lymphocyte responsiveness; these functions do not indicate a utility for diseased states in connection with a decreased hepatic blood flow as according to the present invention.

EXAMPLE 1

Materials and Methods

Male Fischer 344 rats (n=24, 240–260 g, Harlan CPB, Zeist, NL) were maintained in accordance with the recommendations of the Guide for the Care of Laboratory Animals. After acclimatisation to the laboratory environment for 5 days, rats were housed individually and subjected to a 12 hrs. light/dark cycle at controlled environmental conditions. Prior to the experiment, a three days period was taken for nutritional adaptation to the pulverized standard rat chow (SRM-A, Hope Farms, Woerden, NL). Rats were then randomized to receive either a glutamine supplemented enteral diet (n=12) or an isocaloric, isonitrogenous control diet (n=12) for 14 days. The glutamine enriched diet was prepared by adding 12.5% (w/w) L-glutamine powder to the pulverized standard rat chow. In the control diet, glutamine was replaced by the following aminoacids: asparagine (ASN, 3.3%), serine (SER, 2.4%), glycine (GLY, 3.9%), proline (PRO, 2.6%) and alanine (ALA, 2.0%) to balance the nitrogen and caloric content of the glutamine supplemented diet. These non-essential aminoacids have been used in studies investigating several effects of glutamine metabolism; alanine was chosen to compensate for glutamine induced intestinal alanine synthesis. Food intake and urinary output were recorded daily. Body weights were recorded on day 1, 5, 10 and 14. Samples were taken from the 24 hrs urine collections of days 1, 4, 7, 9, 11 and 14 for nitrate determination. Blood flow measurements were performed during the morning of the fifteenth day; until that time, the rats were allowed their respective diets.

Hemodynamic measurements: Blood flow measurements were performed using the radiolabeled microsphere method as previously described (ref's 1, 2). Briefly, on the morning of the fifteenth day animals were anesthetized using Ketamine HCl (50 mgkg$^{-1}$ i.p.) and placed in the supine position on a heating pad that maintained rectal temperature at 37° C. The trachea was intubated with a small piece of polyethylene tubing (PE-240, Fischer, Scientific, Springfield, N.Y., USA) to facilitate breathing. The right carotid artery and left femoral artery were cannulated using PE-50 tubing. Both catheters were connected to P23Db Statham pressure transducers to monitor placement of the carotid catheter into the left cardiac ventricle and to measure femoral artery blood pressure.

Following these procedures, rats were allowed to stabilize for 20 minutes prior to microsphere injection.

Microspheres labeled with $^{46}$Sc were suspended in 0.9% NaCl with two drops of 0.05% Tween-80. The microspheres were ultrasonicated and thoroughly mixed with a Vortex shaker prior to injection. The microsphere vial was placed in a specially adjusted small electromagnetic motor and a magnetic stirring rod in the vial assured continuous mixing of the microspheres during the injection. A 0.7 ml suspension containing 1.0–1.5×10$^5$ microspheres was injected in the left ventricle over a 20 sec. period, and a reference blood sample was obtained from the femoral artery by a callibrated roller pump starting 5 sec. before microsphere injection at a rate of 0.50 ml.min$^{-1}$ for 90 seconds. Following the microsphere procedures, arterial blood was drawn from the aorta for determinations of plasma levels of glutamine, urea, creatinine, ammonia and glucagon. The animals were killed by an intra-arterial injection of pentobarbital sodium (100 mg kg$^{-1}$). After verification of the position of the left ventricular catheter and inspection of the interventricular septum, organs were removed for measurements of radioactivity. Mesenteric fat and superfluous tissue was removed from the organs. Blood flow to the skin and muscle tissue was not measured. The gastrointestinal organs were emptied of their contents. From stomach to colon the presence of digested food substances was confirmed in all the animals investigated. Organs were wrapped in tissue paper and dried under pressure of a 200 g for 15 sec. to remove superfluous extracellular fluid (ref. 3). The organs were weighed and placed in counting vials. The larger organs were divided in portions of ±2 g to assure good geometric distribution within the counting vials. Radioactivity was counted in a well type gamma counter (Type LKB-1280, Ultrogamma, Wallac, Turku, Finland). Count rates were corrected for natural background and counter dead time. Organ blood flows (F) and cardiac output were computed according to the 'reference organ' technique (ref. 2). Organ blood flow was calculated using the equation: F=Fa (Qo/Qa), where Fa is reference flow, Qo is the count rate in the organ and Qa is the count rate in the reference blood sample. Reference flow was computed from the weight of blood in the sampling syringe and the duration of withdrawal, assuming a whole blood density of 1.069 g/ml. Portal venous flow was computed as the sum of the arterial flows through the splanehnic organs i.e. the stomach, pancreas, spleen, small intestine and colon. Hepatic arterial and potal flows were summed to obtain total liver flow. Cardiac output (CO) was calculated according to the equation: CO=Fa (Qtot/Qa), where Qtot is the total injected radioactivity determined by subtracting residual activity in the catheter and injection vial from the initially recorded activity. Qa is the activity in the reference sample and Fa is reference flow.

Blood sampling and chemical blood analysis: Prior to microsphere injection, blood samples (50 $\mu$l) were drawn from the femoral artery catheter for hematocrit and pH determination. To determine acid base balance, pH was measured as part of a blood gas analysis using a commercial blood gas analyzer (ABL 330, Radiometer, Copenhagen, DK). Hematocrit was measured using a microhematocrit reader. For glutamine determination, heparinized arterial blood samples (1 ml) were immediately placed on ice and centrifuged at 1500 g for 10 minutes at 4° C. (Sorval GLC 2 centrifuge, Sorvall Operations, DuPont, Newton, CN, US). Plasma was deproteinized with sulfosalicylic acid (4 mg 100 $\mu$l$^{-1}$) and put in liquid nitrogen. Samples were stored at −70° C. prior to analysis. Glutamine levels were determined by high performance liquid chromatography and pre-column derivatization with ortho-phthaladehyde reagent containing 3-mercaptopropionic acid as recently described (ref. 4).

Aliquots of the arterial plasma samples were used for urea, creatinine and ammonia determination by standard enzymatic methods.

Glucagon assay: Two radioimmunoassays were performed to determine plasma glucagon levels in eight rats of each dietary group as described earlier (ref. 5). One assay determined total glucagon immunoreactivity, using a N-teminally reacting antiserum R59, the other detected pancreatic glucagon, using a specific C-terminally reacting antiserum, RCS5. Enteroglucagon was obtained by subtracting the levels of pancreatic glucagon from total glucagon levels. Changes of 10 pmol/L could be detected with 95 percent confidence.

Nitrate assay: Nitrate ($NO_3^-$) was determined in samples taken from both diets and in samples from 24 hours urine collections. Samples taken from the control and glutamine supplemented diet were diluted 1:5 (w/v) with 80% ethanol, incubated in a shaking water bath for 3 hr at 50° C. and centrifuged for 5 min. at 10,000 g and 4° C., the supernatant was decanted and analyzed for nitrate content. Samples taken from the 24 hours urine collections of day 1, 4, 7, 9, 11 and 14 were also assayed for nitrate content. Nitrate was determined after enzymatic conversion of $NO_3^-$ to nitrite with nitrate reductase from Aspergillus (Bochringer, Mannheim, Del.). The nitrite formed was quantitated by the calorimetric reaction according to Griess (ref. 6). For determining $NO_3^-$ levels in urine samples, urine was diluted 20 times with bidistilled water. To 0.1 ml of diluted urine 0.5 ml phosphate buffer (pH 75, 35 mM), 0.05 ml nitrate reductase 1 mu/L and 0.05 ml NADPH (1.8 mM) were added and the reaction mixture was incubated at room temperature for 2 hours. Excess NADPH, which interferes with the Griess reaction, was then oxidized by adding 0.05 ml phenazine methosulfate (8 nM). For the Griess reaction, 0.25 ml sulfanil reagens (0.1 M sulfanilamide in 1.5 M phosphoric acid) and 0.25 ml N-(1-naphtyl)ethylenediamine (8 mM) were added. After 15 minutes at room temperature, samples were measured at 540 nm in a Vitalab 20 colorimeter (Vital Scientific, NL). The assay was standardized with potassium nitrate solutions ranging from 20 to 200 $\mu$mol/L. The detection limit of the assay was 0.4 $\mu$mol/L, and the recovery of known amounts of nitrate standards added to control urine samples was 99.7±3.1% (mean±SD).

Staistical analysis: All results are means±SEM. Significant differences between means were determined using Student's T test (two-tailed). A p value <0.05 was considered statistically significant.

Results

General: No significant differences in body weights were found between the groups on any of the recorded days, and growth rates were comparable to rats of the same age that were fed normal rat chow. The mean daily food intake (18.6±0.3 g) and mean daily caloric intake (84.7±0.8 kcal) of control rats compared to glutamine supplemented rats (19.0±03 g and 86.3±1.1 kcal per day, respectively) were not significantly different. No differences were observed in mean daily urinary output between control and glutamine group (18.0±0.6 and 18.3±0.6 ml per day). Glutamine plasma levels were significantly higher in glutamine supplemented rats (788±23 $\mu$mol/l) compared to control rats (668±25 $\mu$mol/l) (p<0.005). No significant differences were found in hematocrit, arterial blood pH and $pCO_2$ values and plasma levels of creatinine and urea between glutamine supplemented and control rats.

Hemodynamic data: Reliability of microsphere injections was evaluated using the criteria of Hernandez et al. (ref. 3). Differences in total counts per minute for both kidneys was <6%, evidencing good microsphere mixing and distribution. None of the animals had high lung counts indicating an intact interventricular septum. Differences between blood pressure recordings before and after microsphere injection never exceeded a level of 6 mmHg. No differences between the groups were noted for any of the measured (cardiac output, mean arterial pressure and heart rate), nor for calculated systemic hemodynamic parameters (total peripheral resistance, stroke volume and cardiac index). No differences were noted in organ wet weights between the animals fed the control and those receiving the glutamine supplemented diet. In the glutamine enriched group, significantly higher blood flows were measured in the stomach, the pancreas, the small intestine and colon either expressed as $ml.min^{-1}$ or as $ml.min^{-1}g^{-1}$ wet weight. In addition, calculated splanchnic blood flow (stomach+pancreas+spleen+small intestine+colon) and total hepatic blood flow (splanchnic+hepatic arterial) were calculated and were significantly higher in rats fed the glutamine enriched diet (Table 1).

In the animals fed the glutamine enriched diet, significantly higher percentages of cardiac output were distributed to the stomach (+66%), pancreas (+42%), small intestine (+56%) and colon (+67%). As a result, in glutamine supplemented animals, significantly higher percentages of cardiac output were distributed to the splanchnic organs as a whole (control vs glutamine: 14.95±1.41 vs 22.24±1.17; p<0.0005) and to the liver (sum of splanchnic and hepatic arterial flow; control vs glutamine: 18.00±1.47 vs 25.47±1.09=+42%; p<0.001).

TABLE 1

| organ or tissue | organ flow, ml/min | | flow, ml/min. g | |
| --- | --- | --- | --- | --- |
| | control | glutamine | control | glutamine |
| brain | 0.59 ± .05 | 0.52 ± .06 | 0.45 ± .05 | 0.45 ± .04 |
| heart | 3.83 ± .53 | 3.10 ± .41 | 4.49 ± .66 | 4.01 ± .49 |
| lungs | 0.85 ± .19 | 0.66 ± .16 | 0.79 ± .22 | 0.63 ± .16 |
| diaphragm | 0.27 ± .05 | 0.27 ± .01 | 0.21 ± .02 | 0.23 ± .01 |
| liver (A. hep.) | 2.09 ± .21 | 2.18 ± .30 | 0.34 ± .05 | 0.33 ± .02 |
| stomach | 0.57 ± .06 | 0.86 ± .07 | 0.44 ± .06 | 0.70 ± .06 |
| spleen | 1.01 ± .27 | 1.01 ± .13 | 1.48 ± .16 | 1.61 ± .08 |
| pancreas | 0.77 ± .06 | 1.04 ± .10 | 0.92 ± .14 | 1.31 ± .15 |
| small intestine | 7.02 ± .63 | 9.23 ± .43 | 2.37 ± .18 | 3.47 ± .29 |
| colon | 1.86 ± .16 | 2.89 ± .19 | 1.13 ± .07 | 1.81 ± .23 |
| kidneys | 11.9 ± 1.0 | 11.2 ± 0.9 | 5.55 ± .41 | 5.16 ± .40 |
| splanchnic | 11.5 ± 1.1 | 15.0 ± 0.7 | | |
| total hepatic | 13.6 ± 1.1 | 17.3 ± 0.6 | | |

Glucagon measurements: No differences were observed in plasma levels of pancreatic glucagon and total glucagon between the glutamine supplemented and control dietary group.

Nitrate measurements: Both the control and glutamine enriched diets were analyzed for $NO_3^-$ content using four samples of each of the two diets. Mean nitrate content was 1.71±0.08 and 1.68±0.01 $\mu$mol/g for the control and glutamine enriched diet, respectively (n.s.). On days 4, 7, 9 and 11 $NO_3^-$ production was slightly higher in rats fed the glutamine enriched diet compared to control animals; however, this difference did not reach statistical significance. Mean daily $NO_3^-$ production was calculated and showed no significant differences between the glutamine supplemented and control group.

Disscussion

The present example demonstrates that, compared to an isonitrogenous, isocaloric control diet, a glutamine enriched enteral diet increases splanchnic blood flow by increasing blood flow to the stomach, small intestine, colon and pancreas, and increases total hepatic blood flow by about 27%. Growth rates and mean daily food and calory intake were similar for both groups, indicating that the diets were nutritionally comparable. The calculated mean enteral daily intake of glutamine approximated 2.4 g., which was higher than the daily amount administered by a 2% glutamine enriched parenteral nutrition (1.0–1.8 g.), used in several studies (refs 7, 8). However, the animals fed the 12.5% glutamine enriched diet, showed no signs of metabolic derangements due to increased levels of ammonia and urea, the potentially toxic endproducts of glutamine metabolism. In the present study, the composition of the glutamine enriched and control diet only differed in their relative aminoacid contents. Therefore, changes in splanchnic blood flow were not due to differences in fat or carbohydrate content. The supplemented glutamine in the experimental diet was replaced by ASN, SER, GLY, PRO and ALA in the control diet. These five non-essential aminoacids have been reported not to influence local jejunal blood flow at high postprandial luminal concentrations (ref. 9). Thus, the increase in splanchnic blood flow in rats fed the glutamine enriched diet can only be attributed to glutamine supplementation.

The increases in blood flows to the gastrointestinal organs in the animals fed the glutamine enriched diet occurred in the absence of any changes in cardiac output resulting in greater percentages of cardiac output distributed to each of these organs compared to rats fed the control diet. This indicates that the increased blood flows to the splanchnic organs in the glutamine fed group is based on local vasodilatory responses. No differences in arterial pancreatic glucagon plasma levels were noted between the rats fed the control and glutamine enriched diet, indicating that the glutamine induced increases in splanchnic blood flow upon enteral administration were not mediated by glucagon. The mean daily $NO_3^-$ production was not different between the control and glutamine group, suggesting that NO production did not play a role in the splanchnic vasodilatory response to glutamine.

In conclusion, the present example shows that compared to a balanced control diet, a glutamine enriched enteral nutrition increased splanchnic blood flow, and thus total hepatic blood flow in the rat. The increases in organ blood flow were not mediated by an increased production of pancreatic glucagon or nitric oxide as determined by urinary nitrate excretion. These findings are of clinical importance.

EXAMPLE 2

This example provides evidence that glutamine-supplemented enteral nutrition increases renal arginine production by providing increased levels of circulating citrulline to the kidneys. Thus glutamine enriched enteral nutrition in the rat significantly increases arterial arginine plasma levels by increasing renal arginine production.

Materials and Methods

General: Rats were maintained and fed as in Example 1.

Kidney blood flow measurement and blood sampling: Kidney blood flow measurements were performed using the radiolabeled microsphere method as descrbed in Example 1. Following blood flow measurement the abdomen was opened and the left renal vein was cannulated using a 12 gauge needle attached to a heparinized syringe. The renal vein was clipped at its entrance into the caval vein and a blood sample (1 ml) was drawn. An additional blood sample was drawn from the abdominal aorta. Rats were killed by an overdose of sodium pentobarbital (100 mgkg$^{-1}$). After verification of the position of the left ventricular catheter the kidneys were removed, weighed and placed in counting vials. Radioactivity and organ blow flow measurements were performed as in Example 1.

Aminoacid and chemical blood analysis: Blood samples were immediately placed on ice. After centrifugation at 3000 rpm for 10 min. at 4° C., aliquots of plasma were pipetted in cryo-vials containing crystallized sulfosalicylic acid (4 mg/100 $\mu$l), immediately Vortex mixed and put in liquid nitrogen. Samples were stored at −70° C. until aminoacid determination. Aminoacids involved in arginine synthesis were determined in plasma using HPLC. Aliquots of the arterial plasma samples were used for ammonia and urea determination by standard enzymatic methods.

Calculations: Net aminoacid fluxes over the kidneys were computed by the following equation: Net kidney flux (nmolml$^{-1}$min$^{-1}$)=([A]−[RV])×F, where [A] represents the arterial plasma aminoacid concentration, [RV] the plasma aminoacid concentration in the renal vein and F plasma flow through both kidneys (the sum of the left and right kidney plasma flows). According to this method a minus sign indicates release. Net extraction rate (Enet) was calculated as follows: [A]−[RV]/[A].

Statistical Analysis:

All results are means±SEM. Significant differences between means were determined using Student's T test. A p value <0.05 was considered statistically significant.

Results

General: There were no statistical significant differences in body weights between the rats in the glutamine supplemented and control group on any of the recorded days (cf. Example 1). Total kidney weights (sum of left and right kidneys) were not different between the control and glutamine group (2.17±0.03 and 2.19±0.07 g resp.). No significant differences in haematocrit, arterial pH and arterial plasma concentrations of ammonia and urea was found between rats fed the glutamine supplemented and control diet.

Kidney aminoacid handling: Table 2 shows the results of arterial and renal venous plasma aminoacid determinations, A-RV differences, net kidney flux and net extraction calculations. There was no difference in total kidney plasma flow between the glutamine and control group (5.57±0.27 and 5.71±0.28 mlmin$^{-1}$ resp.). The animals fed the glutamine enriched diet showed significantly higher mean arterial plasma concentrations of glutamine (17%), arginine (31%) and citrulline (30%). Significantly higher renal venous plasma concentrations of glutamine (6%), citrulline (22%) and arginine (31%) were detected in the glutamine enriched group. Flux calculations showed a significantly higher uptake of circulating glutarmine (306%), aspartate (318%) and citrulline (40%) by the kidneys of rats fed the glutamine enriched diet. The release of arginine by the kidney was significantly higher (38%) in the glutamine fed rats. In the glutamine fed animals net extraction rates of the kidneys for glutamine and aspartate significantly increased. No changes in net extraction rates were observed for glutamate, citrulline, arginine and omithine. A highly significant correlation between citrulline uptake and arginine release by the kidneys was found in both the control group and glutamine group (r=0.84; p<0.0001 and r=0.83; p<0.0001 resp.).

TABLE 2

Glutamine enriched diet: the effect on kidney aminoacid handling

| | A | | RV | | A-RV | |
|---|---|---|---|---|---|---|
| | Control | Glutamine | Control | Glutamine | Control | Glutamine |
| GLN | 668.5 ± 25.1 | 788.4 ± 22.6[#] | 646.5 ± 20.0 | 688.1 ± 29.0 | 23.8 ± 22.0 | 99.3 ± 14.1[**] |
| GLU | 58.3 ± 6.1 | 67.8 ± 6.6 | 52.9 ± 3.2 | 59.7 ± 3.2 | 4.7 ± 4.8 | 12.2 ± 5.3 |
| ASP | 5.9 ± 0.5 | 7.2 ± 1.1 | 3.7 ± 0.9 | 2.8 ± 0.6 | 1.3 ± 0.7 | 4.4 ± 1.2[*] |
| ARG | 86.8 ± 4.4 | 113.7 ± 4.8[!] | 110.1 ± 3.6 | 145 ± 5.6[!!] | −23.9 ± 3.1 | −32.4 ± 3.7[*] |
| CIT | 48.1 ± 1.3 | 62.7 ± 2.1[!!] | 25.5 ± 1.5 | 30.3 ± 1.3[] | 22.6 ± 2.5 | 32.4 ± 2.3[] |
| ORN | 30.0 ± 1.9 | 33.4 ± 1.9 | 31.0 ± 1.4 | 33.7 ± 1.8 | −1.0 ± 1.4 | −0.3 ± 0.9 |

| | Kidney flux | | Enet kidney | |
|---|---|---|---|---|
| | Control | Glutamine | Control | Glutamine |
| GLN | 136.0 ± 139.1 | 553.2 ± 89.1[*] | 0.03 ± 0.03 | 0.13 ± 0.02[**] |
| GLU | 28.9 ± 30.1 | 65.9 ± 29.0 | 0.03 ± 0.07 | 0.12 ± 0.06 |
| ASP | 5.8 ± 2.8 | 24.3 ± 6.4[*] | 0.2 ± 0.1 | 0.6 ± 0.1[*] |
| ARG | −131.4 ± 18.0 | −181.6 ± 18.2[*] | −0.29 ± 0.04 | −0.29 ± 0.03 |
| CIT | 128.9 ± 14.8 | 180.7 ± 16.3[*] | 0.47 ± 0.04 | 0.51 ± 0.03 |
| ORN | −5.7 ± 8.1 | −1.7 ± 5.0 | −0.03 ± 0.05 | −0.01 ± 0.03 |

Data are expressed in nmolml$^{-1}$ (A, RV, and A-RV) and nmolmin$^{-1}$ (Kidney flux) and as means ± SEM.
A and RV represent arterial and renal venous plasma aminoacid concentrations.
Enet kidney is netto extraction rate of aminoacids by the kidney.
Number of observations is 12 in each group.
Statistical analysis by Students T test.
Significances are indicated as follows:
[*]$p < 0.05$,
[**]$p < 0.01$,
[#]$p < 0.005$,
[##]$p < 0.005$,
[!]$p < 0.0005$ and
[!!]$p < 0.0001$.

References

1. Van Leeuwen, P. A. M., J. R. Bading, N. A. Vydelingum, R. N. Younes, P. de Rooij, and M. Brennan. *J. Appl Physiol.* 71(5): 1674–1678, 1991.
2. Malik, A. R., J. E. Kaplan, and T. M. Saba. *J. Appl. Physiol.* 40: 472–475, 1976.
3. Hernandez, L. A., P. R. Kvietys, and D. N. Granger. *Am. J. Physiol.* 251 (Gastrointest. Liver Physiol. 14): G117–G123, 1986.
4. Teerlink, T., M. W. T Hennekes, P. A. M. van Lecuwen, and A. P. J. Houdijk. *Clinica Chimica Acta* 218: 159–168, 1993.
5. Thomson, J. P. S., and S. R. Bloom. *Clin. Sci. Mol. Med.* 51: 177–183, 1976.
6. Green, L. C., D. A. Wagner, J. Glogowski, P. L. Skipper, J. S. Wishnok, and S. R. Tannenbaum. *Anal. Biochem* 126: 131–138, 1982.
7. Li, S. L., M. S. Nussbaum, D. W. McFadden, F-S. Zhang, R. J. LaFrance, R. Dayal, and J. Fischer. *J. Surg. Res.* 48: 421–426, 1990.
8. Yoshida, S., M. J. Leskiw, M. D. Sclutter, K. T. Bush, R. G. Nagele, S. Lanza-Jacoby, and T. P. Stein. *Am. J. Physiol.* 263: (Endocrinol. Metab. 26): E368–E373, 1992.
9. Chou, C. C., P. Kvietys, J. Post, and S. P. Sit. *Am. J. Physiol.* 235(6): H677–H682, 1978.

We claim:

1. A method for the treatment of a diseased state which is associated with low arginine plasma levels, comprising enterally administering an amount of glutamine or a glutamine equivalent to a subject suffering from such a state such as to provide a daily glutamine dosage of 0.2–4 g/kg body weight per day, said state being systemic inflammation, high plasma arginase level, bacteremia, jaundice, liver transplantation, increased cytokine production or liver steatosis.

2. A method according to claim 1, further comprising enterally administering an amount of arginine or an arginine equivalent such as to provide a daily arginine dosage of up to 4 g/kg body weight.

3. A method according to claim 1, comprising enterally administering 16–150 g of glutamine or a glutamine equivalent per day.

4. A method according to claim 1, further comprising administering to said subject at least one of at least 10 g of vegetable fibers and at least 5 g of inulin per daily dosage.

* * * * *